United States Patent
Mishima

(10) Patent No.: US 7,762,962 B2
(45) Date of Patent: Jul. 27, 2010

(54) INTERMEDIATE MEMBER, AND A MEDICAL DEVICE AND GUIDE WIRE INCLUDING SUCH AN INTERMEDIATE MEMBER

(75) Inventor: Katsuro Mishima, Yugawara-cho (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 0 days.

(21) Appl. No.: 12/013,113

(22) Filed: Jan. 11, 2008

(65) Prior Publication Data

US 2008/0171952 A1   Jul. 17, 2008

Related U.S. Application Data

(60) Provisional application No. 60/880,711, filed on Jan. 17, 2007.

(30) Foreign Application Priority Data

Jan. 12, 2007   (JP)   ............... 2007-005002

(51) Int. Cl.
*A61M 25/00*   (2006.01)
(52) U.S. Cl. .................................... 600/585
(58) Field of Classification Search ................ 600/434, 600/435, 585; 604/164.13
See application file for complete search history.

(56) References Cited

U.S. PATENT DOCUMENTS 4,456,481 A * 6/1984 McGinniss ................ 420/443
4,925,445 A   5/1990 Sakamoto et al.
5,069,226 A   12/1991 Yamauchi et al.
5,238,004 A   8/1993 Sahatjian et al.
5,269,759 A   12/1993 Hernandez et al.
5,354,623 A   10/1994 Hall
5,368,049 A   11/1994 Raman et al.
5,402,799 A   4/1995 Colon et al.
5,411,476 A   5/1995 Abrams et al.
5,452,726 A   9/1995 Burmeister et al.
5,497,786 A   3/1996 Urick
5,498,250 A   3/1996 Prather
5,695,111 A   12/1997 Nanis et al.

(Continued)

FOREIGN PATENT DOCUMENTS

JP   1-124473 A   5/1989
JP   2006-150146 A   6/2006

OTHER PUBLICATIONS http://www.espimetals.com/tech/inconel625.pdf.*
http://www.science.co.il/PTelements.asp?s=ionization. Jun. 25, 2009.*

*Primary Examiner*—Max Hindenburg
*Assistant Examiner*—Jonathan M. Foreman
(74) *Attorney, Agent, or Firm*—Buchanan Ingersoll & Rooney PC

(57) ABSTRACT

An intermediate member is disposed between a first member made of a first metal material and a second member made of a second metal material having a different composition from that of the first metal material. The intermediate member is welded to the first member and the second member to connect the first member and the second member to each other. The intermediate member contains at least one metal component, wherein the metal component is Pd, Pt, Rb, Ir or Ta.

18 Claims, 5 Drawing Sheets

U.S. PATENT DOCUMENTS

| | | |
|---|---|---|
| 5,753,885 A * | 5/1998 | Iwasa et al. ............ 219/118 |
| 5,772,609 A | 6/1998 | Nguyen et al. |
| 5,797,857 A | 8/1998 | Obitsu |
| 5,876,356 A | 3/1999 | Viera et al. |
| 5,924,998 A | 7/1999 | Cornelius et al. |
| 5,951,494 A | 9/1999 | Wang et al. |
| 6,001,068 A | 12/1999 | Uchino et al. |
| RE36,628 E | 3/2000 | Sagae et al. |
| 6,093,157 A | 7/2000 | Chandrasekaran |
| 6,165,292 A | 12/2000 | Abrams et al. |
| 6,234,981 B1 | 5/2001 | Howland |
| 6,352,515 B1 * | 3/2002 | Anderson et al. ........ 600/585 |
| 6,390,992 B1 | 5/2002 | Morris et al. |
| 6,520,923 B1 | 2/2003 | Jalisi |
| 6,602,208 B2 | 8/2003 | Jafari |
| 6,679,853 B1 | 1/2004 | Jalisi |
| 6,702,762 B2 | 3/2004 | Jafari et al. |
| 7,278,974 B2 * | 10/2007 | Kato ..................... 600/585 |
| 2001/0025799 A1 * | 10/2001 | Nishino et al. .......... 205/658 |
| 2004/0030266 A1 | 2/2004 | Murayama et al. |
| 2004/0039308 A1 | 2/2004 | Murayama et al. |
| 2004/0039309 A1 | 2/2004 | Murayama et al. |
| 2004/0106878 A1 * | 6/2004 | Skujins et al. .......... 600/585 |
| 2005/0152731 A1 | 7/2005 | Mishima et al. |

* cited by examiner

INTERMEDIATE MEMBER, AND A MEDICAL DEVICE AND GUIDE WIRE INCLUDING SUCH AN INTERMEDIATE MEMBER

This application claims priority under 35 U.S.C. §119(e) to U.S. Provisional Application No. 60/880,711 filed on Jan. 17, 2007, the entire content of which is incorporated herein by reference. This application is also based on and claims priority to Japanese Application No. 2007-5002 filed on Jan. 12, 2007, the entire content of which is incorporated herein by reference.

TECHNOLOGICAL FIELD

This invention generally relates to an intermediate member interposed between other members and used to connect the other members to each other, and a medical device using the intermediate member. More specifically, the invention pertains to a guide wire used to introduce a catheter into a body cavity such as a blood vessel.

BACKGROUND DISCUSSION

A guide wire is employed to guide a catheter used for treating a site where access to a surgical operation or procedure is difficult such as, for example, PTCA (Percutaneous Transluminal Coronary Angioplasty) or for treating the human body in a minimally-invasive manner, or for examination purposes such as cardiovascular contrast imaging. A guide wire used for PTCA is inserted together with a balloon catheter, in a state in which the distal end of the guide wire projects outwardly from the distal end of the balloon catheter, into a portion in the proximity of a vasoconstrictive site which is a target site.

Blood vessels can have shapes that curve in rather complicated ways. Thus, for a guide wire used when a balloon catheter is inserted into a blood vessel, the guide wire must have flexibility and resilience against suitable flexure, pushability and torque transmission performance for transmitting an operation force at the proximal portion to the distal side (these are generally referred to as "steerability"), kink resistance (flexural resistance) and other characteristics. Possible constructions for obtaining suitable flexibility, among the characteristics mentioned above, include a structure including a metal coil having flexibility against flexure disposed around a thin distal core member of a guide wire, or a structure which includes a superelastic wire of Ni—Ti or the like for a core member of a guide wire in order to provide the guide wire with flexibility and resilience.

A core member of a guide wire is made of substantially one kind of material, and in order to increase the steerability of the guide wire, a material having a comparatively high coefficient of elasticity is used. As a result of this, there the flexibility of the guide wire distal portion tends to be lost. On the other hand, if a material having a comparatively low coefficient of elasticity is used to obtain flexibility of the distal portion of the guide wire, there is a loss in the steerability on the proximal side of the guide wire. It has thus been difficult to achieve both the required flexibility and the required steerability with one kind of core member.

To achieve improvements against drawbacks such as those described above, for example, a guide wire has been proposed in which a first wire disposed on the distal side and having flexibility and a second wire disposed on the proximal side and having high rigidity are connected to each other by soldering.

This guide wire achieves improvement in steerability by increasing the flexibility on the distal side and increasing the rigidity on the proximal side.

However, a solder material itself made of an Ag—Cu based alloy, which is a popularly used material for soldering, is relatively low in mechanical characteristics such as flexural strength. Thus, when the guide wire is curved, there is the possibility that the soldered portion may be broken or bent.

Further, where the first wire and the second wire are individually covered with an oxide film, upon soldering, the oxide film cannot get wet with the solder material. Therefore, it is difficult to firmly solder the first wire and the second wire to each other.

SUMMARY

According to one aspect, a guide wire comprises an elongated wire body and a coil covering at least a distal portion of the elongated wire body, wherein the elongated wire comprising a first wire member and a second wire member that are coaxially positioned relative to one another. The first wire member is made of a metal material, and the second wire member is made of a metal material having a composition different from the composition of the metal material forming the first wire member. The coil is made of a metal material having a composition different from the composition of the metal material forming the first wire member. An intermediate member is disposed either between the first wire member and the second wire member and connecting the first and second wire members to each other, or between the first wire member and the coil and connecting the coil to the first wire member. The intermediate member comprises at least one of Pd, Pt, Rb, Ir and Ta.

According to another aspect, an intermediate member for a medical device is adapted to be positioned between a first member made of a first metal material and a second member made of a second metal material having a different composition from that of the first metal material. The intermediate member is made of a material weldable to the first member and the second member to connect the first member and the second member to each other, with the intermediate member containing at least one metal component, and wherein the one metal component is Pd, Pt, Rb, Ir or Ta.

The total content of the metal component in the intermediate member is preferably 0.1 to 99 atom %. The intermediate member may further contain a material which lowers the melting point of the intermediate member. The material which lowers the melting point of the intermediate member preferably is at least one of Mg, Au, Ag, Cu, Ca and Li.

The first metal material and the second metal material individually may contain at least one of Fe, Ni and Ti. The first metal material is preferably made of a Ni—Ti based alloy. The second metal material preferably is made of stainless steel. The first metal material and the second metal material individually may contain at least one of Ti and Cr as a principal component, and the intermediate member further contains a metal having an ionization tendency higher than that of Ti and Cr. The metal having an ionization tendency higher than that of Ti and Cr is preferably Mg.

The intermediate member can be made of a Pd—Mg alloy, and the content of Mg in the Pd—Mg alloy is preferably 87 to 97 atom %. The intermediate member preferably is made of an Ir—Mg alloy, and the content of Mg in the Ir—Mg alloy is 93 to 99.9 atom %. The melting point of the intermediate member may be 500 to 1,350° C. One of the first member and the second member may be a first wire disposed on the distal side, and the other may be a second wire disposed on the proximal side of the first wire. Alternatively, one of the first member and the second member can be a wire body, and the other is preferably a spiral coil which covers a distal side portion of the wire body.

According to another aspect, a guide wire includes a first member made of a first metal material, a second member made of a second metal material having a different composition from that of the first metal material, and an intermediate member disposed between the first member and the second member. The intermediate member contains at least one metal component selected from Pd, Pt, Rb, Ir and Ta. The first metal material and the second metal material individually may contain at least one of Ti and Cr as a principal component, and the intermediate member may further contain a metal having an ionization tendency higher than that of Ti and Cr. The metal having the ionization tendency higher than that of Ti and Cr preferably is Mg.

BRIEF DESCRIPTION OF THE DRAWING FIGURES

The foregoing and additional features and aspects of the guide wire will become more apparent from the following detailed description considered with reference to the accompanying drawing figures briefly described below.

Figure 1:
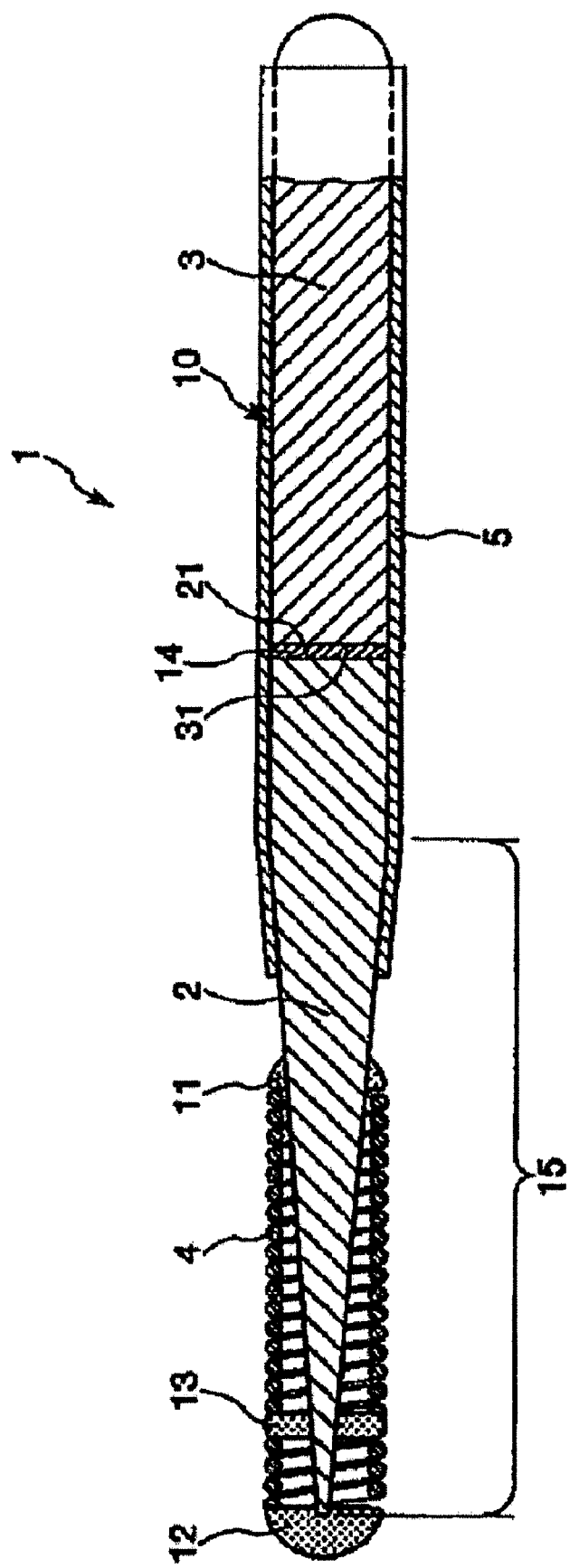
FIG. 1 is a longitudinal cross-sectional view of a first embodiment of a guide wire disclosed herein.
Figure 2:
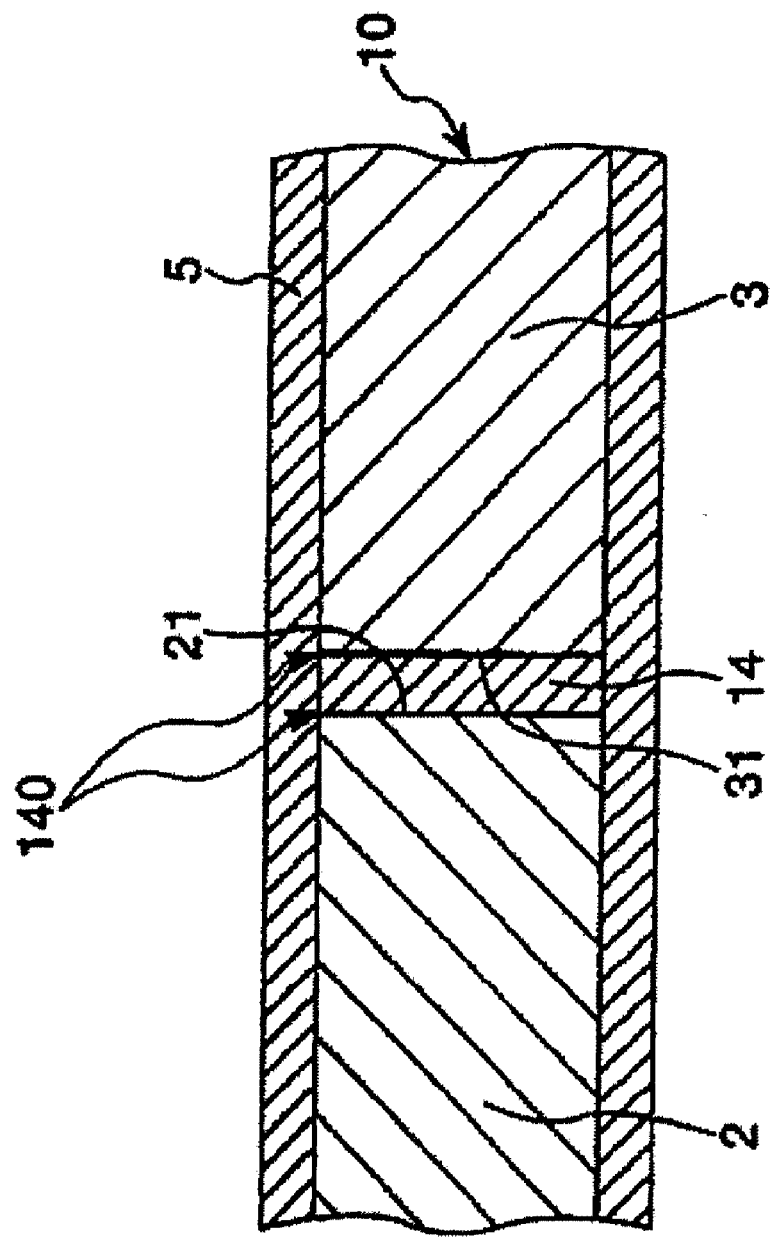
FIG. 2 is an enlarged cross-sectional view of a connection portion of the guide wire shown in FIG. 1.
Figure 3A:
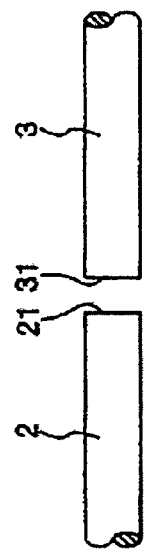
Figure 3B:
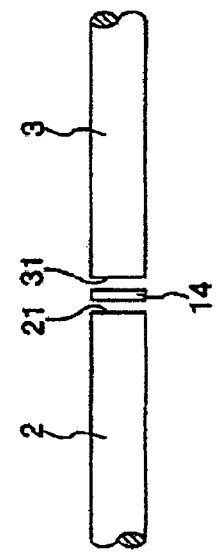
Figure 3C:
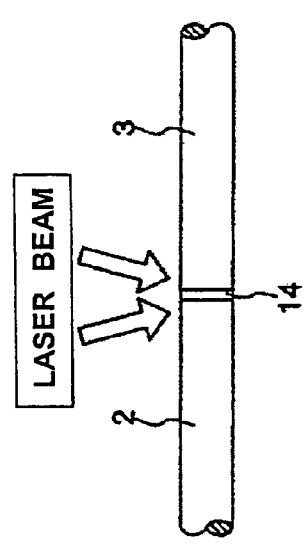
Figure 3D:
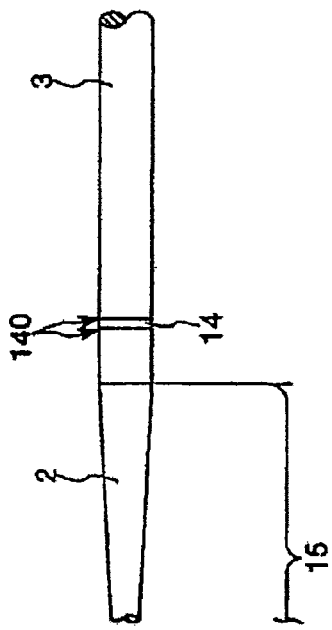

FIGS. 3(a)-(d) are somewhat schematic illustrations showing a procedure of welding a first wire and a second wire of the guide wire shown in FIG. 1 using an intermediate member.

Figure 4:
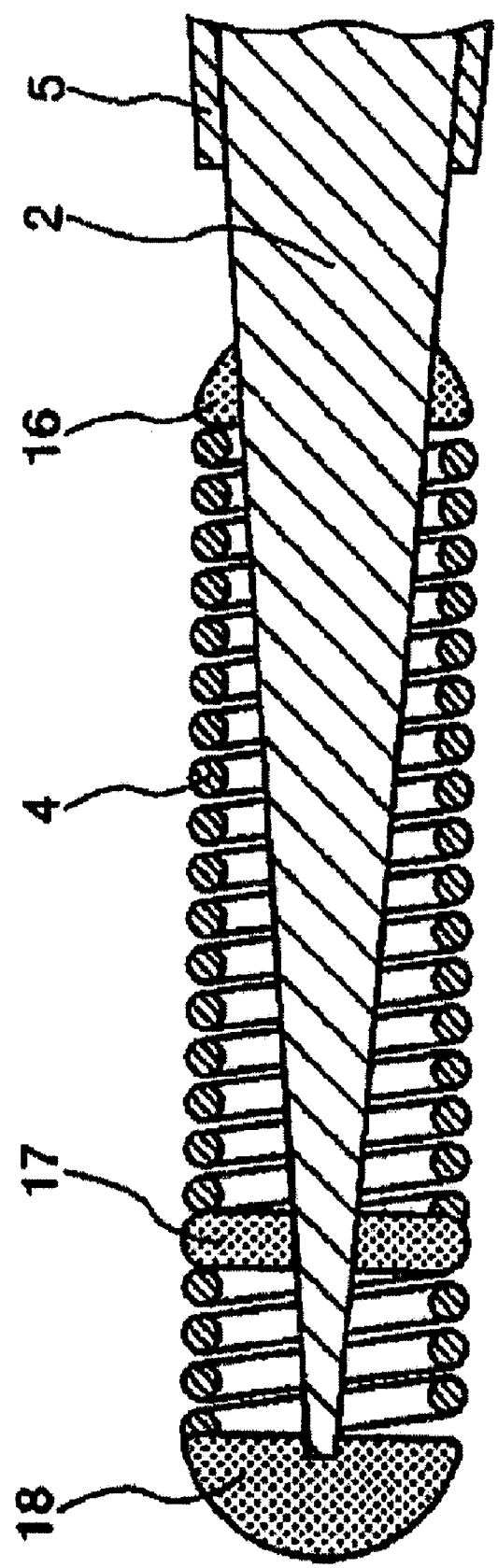

FIG. 4 is an enlarged vertical cross-sectional view of a portion of a guide wire according to a second embodiment.

Figure 5:
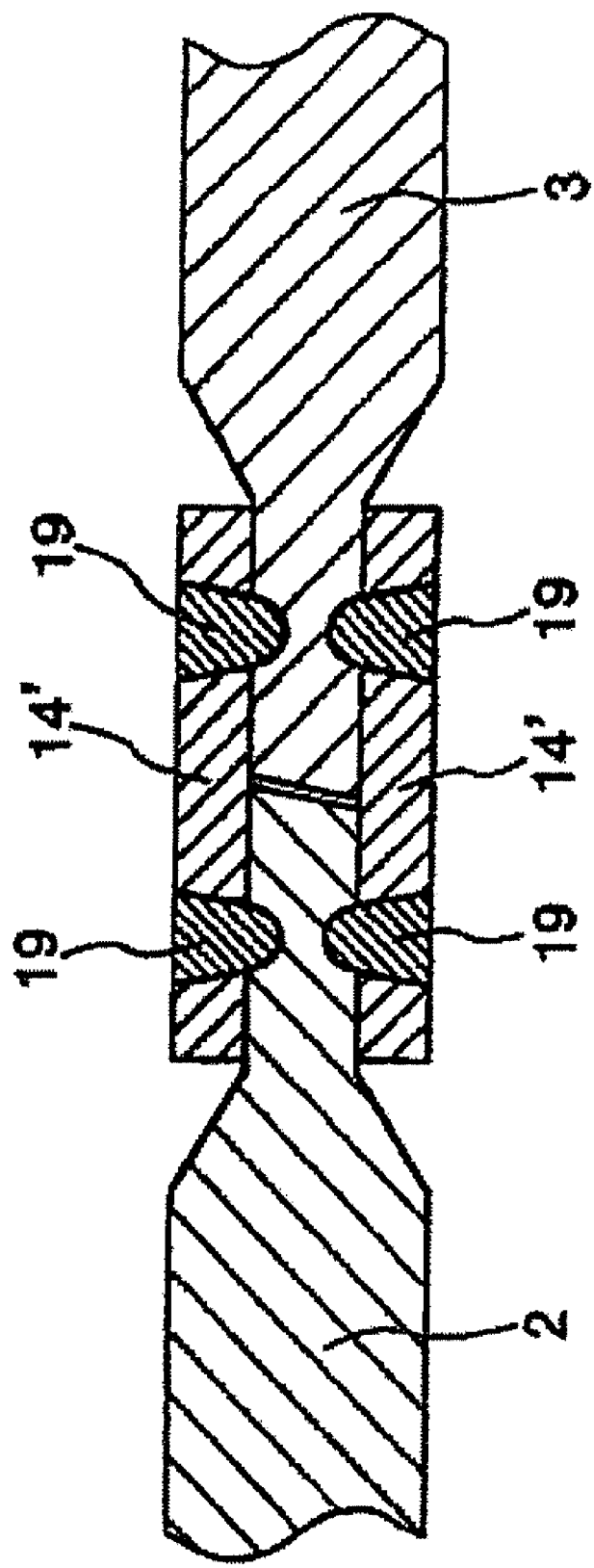

FIG. 5 is an enlarged vertical cross-sectional view of a portion of a guide wire according to a third embodiment.

DETAILED DESCRIPTION

An intermediate member as disclosed herein is adapted to be disposed between a first member made of a first metal material and a second member made of a second metal material, and is adapted to be welded to the first member and the second member so to connect the first member and the second member to each other. The intermediate member disclosed here contains at least one of Pd (palladium), Pt (platinum), Rb (rhodium), Ir (iridium) and Ta (tantalum).

The present embodiment (first embodiment) is described using a first member in the form of a first wire and a second member in the form of a second wire, with the first member being disposed on the distal side and the second member being disposed on the proximal side of the first wire.

It is to be noted that the right side in FIGS. 1 to 4 is referred to as the "proximal" side or end, and the left side is referred to as the "distal" side or end. Further, in FIGS. 1 to 4, in order to facilitate an understanding of the guide wire incorporating the intermediate member, the guide wire is illustrated as being contracted in the lengthwise direction while being exaggerated in the thicknesswise direction. Thus, the ratio between the dimensions in the lengthwise direction and the thicknesswise direction is much different from that of an actual guide wire.

The guide wire 1 shown in FIG. 1 is a guide wire for a catheter which is inserted into and used together with a catheter. The guide wire includes an elongated wire body 10 and a spiral coil 4. The wire body 10 includes a first wire 2 disposed on the distal side and a second wire 3 disposed on the proximal side of the first wire 2. The first and second wires 2, 3 are connected to each other and are coaxial with one another. The total length of the guide wire 1 is not limited to any particular length, but is preferably approximately 200 to 5,000 mm. Further, although the outer diameter of the wire body 10 (the outer diameter of a portion whose outer diameter is fixed or constant) is not particularly limited, the outer diameter of the wire body 10 is preferably approximately 0.2 to 1.2 mm.

The first wire 2 may be formed from a wire rod, preferably a wire rod having elasticity. The length of the first wire 2, though not necessarily limited, is preferably is approximately 20 to 1,000 mm.

In the present embodiment, the first wire 2 has a fixed outer diameter over a predetermined length from the proximal end thereof and has a gradually decreasing outer diameter from an intermediate portion thereof in a direction toward the distal end. This portion with the gradually decreasing or varying outer diameter is referred to as the outer diameter gradually decreasing portion 15. By providing the first wire 2 with such an outer diameter gradually decreasing portion 15 as just described, the rigidity (flexural rigidity, torsional rigidity) of the first wire 2 gradually decreases in the direction toward the distal end. As a result, the guide wire 1 possesses good flexibility at the distal portion thereof, resulting in improvement in trackability and safety for a blood vessel, and also in prevention of bending and so forth.

In the illustrated embodiment, the outer diameter gradually decreasing portion 15 is formed as a part of the first wire 2. That is, the outer diameter gradually decreasing portion 15 extends from an intermediate portion of the first wire 2 to the distal end of the first wire, while the proximal portion of the first wire possesses a constant outer diameter. However, the entire first wire 2 may be configured as the outer diameter gradually decreasing portion 15.

The tapering angle (decreasing ratio of the outer diameter) of the outer diameter gradually decreasing portion 15 may be fixed along the wire longitudinal direction or may partially vary along the longitudinal direction. For example, a portion having a comparatively larger tapering angle (decreasing ratio of the outer diameter) and a portion having a comparatively smaller tapering angle may be formed alternatively and repetitively at a plurality of locations along the first wire 2.

Further, the first wire 2 may be configured to include, intermediately of the outer diameter gradually decreasing portion 15 or on the distal side with respect to the outer diameter gradually decreasing portion 15, a portion having a fixed or constant outer diameter along the longitudinal direction. For example, the first wire 2 may be constructed so that a tapering portion in the form of a taper whose outer diameter gradually decreases in the direction toward the distal end is formed at a plurality of locations along the longitudinal direction and a portion whose outer diameter is constant along the longitudinal direction is formed between adjacent ones of such tapering portions. Also in such an instance as just described, similar effects to those described above can be obtained.

It is also possible to provide a configuration in which the proximal portion of the outer diameter gradually decreasing portion 15 is positioned intermediately of the second wire 3, that is a configuration in which the outer diameter gradually decreasing portion 15 extends across the boundary (intermediate member 14) of the first wire 2 and the second wire 3.

In the present embodiment, the first wire 2 is made principally of a first metal material. Examples of the first metal material include Fe, Ni, Ti, Co, Cr, V, Mn, Nb, Mo, W, Al, Cu, Zn. One or two or more of the metal materials can be used in combination to form the first wire 2. However, particularly from the point of view of mechanical characteristics such as toughness and strength, the first metal material preferably contains at least one of Fe, Ni and Ti.

Further, in the present embodiment, it is particularly preferable for the first metal material to be an alloy which exhibits pseudoelasticity (including a superelastic alloy). More preferably, a superelastic alloy is used. Since the superelastic alloy is comparatively flexible and has resilience and hence is less likely to have a deflection habit (i.e., is less likely to experience a set or maintain a bent shape when deflected), where the first wire 2 is made of a superelastic alloy, the guide wire 1 is provided with sufficient flexibility and resilience against bending at a portion of the distal side thereof. Consequently, the ability to track or follow a blood vessel which is curved and bent in a relatively complicated manner is improved and more excellent steerability is obtained. In addition, even if the first wire 2 is repetitively subjected to curved or bent deformation, the first wire 2 does not have a flexure habit (does not maintain a bent shape) due to its resilience. Therefore, deterioration of the steerability caused by a flexure habit provided to the first wire 2 during use of the guide wire 1 is inhibited or prevented.

Pseudoelastic alloys includes those having any stress-strain curve characteristics by tension, those with which a transformation point as As, Al, Ms or Mf can be measured or determined notably or cannot be measured, and all of those which are deformed (distorted) by a great amount by stress and almost restore its original shape when the stress is removed.

Preferable examples of compositions of such a superelastic alloy as described above include a Ni—Ti based alloy such as a Ni—Ti alloy containing 49 to 52 atom % Ni, a Cu—Zn alloy containing 38.5 to 41.5 weight % Zn, a Cu—Zn—X alloy containing 1 to 10 weight % X (X is at least one of Be, Si, Sn, Al and Ga), a Ni—Al alloy containing 36 to 38 atom % Al. Among these, the Ni—Ti based alloy is particularly preferable. Where a Ni—Ti based alloy is used as the first metal material, the flexibility and the resilience of the distal side of the guide wire 1 is enhanced. It is to be noted that a superelastic alloy represented by a Ni—Ti based alloy is superior also in adhesive properties of a coating layer 5 hereinafter described.

The distal end of the second wire 3 is connected or joined to the proximal end of the first wire 2 by welding through an intermediate member 14. Although the second wire 3 may be any wire, a wire having elasticity is particularly preferable. Further, although the length of the second wire 3 is not necessarily limited, it is preferably approximately 20 to 4,800 mm.

Further, in the present embodiment, the second wire 3 is preferably made of a material having a coefficient of elasticity (Young's modulus (modulus of vertical elasticity) and a modulus of rigidity (horizontal elasticity), modulus of volume elasticity) higher than those of the first metal material. Suitable rigidity (flexural rigidity, torsional rigidity) is thus imparted to the second wire 3, and the guide wire 1 exhibits increased flexural strength and improved pushability and torque transmission performance. Consequently, more excellent insertion steerability is obtained.

In this embodiment, the second wire 3 is made of a second metal material having a different composition from that of the first metal material forming the first wire 2. Examples of the second metal material for the second wire 3 include Fe, Ni, Ti, Co, Cr, V, Mn, Nb, Mo, W, Al, Cu, Zn. One or two or more of the metal materials can be used in combination. However, standpoint of mechanical characteristics such as toughness and strength, the second metal material preferably contains at least one of Fe, Ni and Ti.

Further, in the present example, the second metal material can be various metal materials such as stainless steel, piano wires, cobalt based alloys and pseudoelastic alloys particularly such as SUS304, SUS303, SUS316, SUS316L, SUS316J1, SUS316J1L, SUS405, SUS430, SUS434, SUS444, SUS429, SUS430F and SUS302.

Among these materials, the cobalt based alloys have a high coefficient of elasticity when they are formed into a wire and have a suitable elastic limit. Therefore, the second wire 3 made of a cobalt based alloy has a particularly excellent torque transmission performance and very seldom suffers from a problem of buckling or the like. As the cobalt based alloy, any cobalt based alloy which contains Co as a component element may be used. Preferably, a cobalt based alloy containing Co as a main component (i.e., a Co base alloy in which the content of Co is highest in weight ratio among the elements which compose the alloy) is used, and more preferably a Co—Ni—Cr based alloy is used. Where an alloy having such a composition as described above is used as the second metal material, the effects described hereinabove become more noticeable. Further, since an alloy of such a composition as described above has plasticity also in deformation at a room temperature, it can be deformed rather readily into a desired shape, for example when during use or the like. Further, since an alloy of such a composition as described above has a relatively high coefficient of elasticity and a relatively high elastic limit so as to allow cold forming, miniaturization can be achieved while also sufficiently inhibiting or preventing the occurrence of buckling, and flexibility and rigidity sufficient for insertion into a predetermined site is realized.

By way of example, the Co—Ni—Cr based alloy is preferably an alloy having a composition of 28 to 50 weight % Co-10 to 30 weight % Ni-10 to 30 weight % Cr-remaining Fe, including an alloy wherein part of the alloy mentioned is substituted by another element (substitution element). The inclusion of the substitution element exhibits a unique effect in accordance with the type of substitution element. For example, where at least one element selected from Ti, Nb, Ta, Be and Mo is used as the substitution element, further improvement of the strength of the second wire 3 and so forth can be anticipated. It is to be noted that, where an element other than Co, Ni and Cr is contained, preferably the content of the element (the entire amount of the substitution element or elements) is lower than 30 weight %.

Further, part of the Co and Ni may be substituted by another element. For example, part of the Ni may be substituted by Mn. In this alternative, further improvement in workability or the like can be anticipated. Further, among Co—Ni—Cr based alloys, a Co—Ni—Cr—Mo based alloy which contains Mo is particularly preferable.

Further, where stainless steel is used as the second metal material, the guide wire 1 is provided with more excellent pushability and torque transmission performance.

As a particular combination of the first wire 2 and the second wire 3, it is particularly preferable to form the first wire 2 from a Ni—Ti based alloy and to form the second wire 3 from a Cu—Ni—Cr based alloy or stainless steel. With this combination, such effects as the pushability and the torque transmission performance as described above become further noticeable.

In the illustrated embodiment, the second wire has an outer diameter that is constant over its entire length. However, it is also possible for the second wire 3 to have a portion whose outer diameter varies along the longitudinal direction.

Further, while the illustrated embodiment includes the first wire 2 and the second wire 3 connected to each other to form the wire body 10, the wire body 10 may otherwise be formed from three or more wires or wire rods connected to each other.

The coil 4 is a member constructed as a spirally wound wire rod (thin wire) and is positioned in such a manner as to cover the distal side portion of the first wire 2. In the configuration shown, the distal side portion of the first wire 2 is positioned in the central portion of the inside of the coil 4 (i.e., the distal end portion of the first wire 2 is centrally located within the coil 4 so that the distal end portion of the first wire 2 and the coil 4 are coaxial). Further, the distal side portion of the first wire 2 is positioned within the coil 4 without contacting the inner surface of the coil 4. An intermediate member 14, described in more detail below, is positioned on the proximal side with respect to the distal end of the coil 4.

In the illustrated embodiment, the coil 4 is constructed so that a small gap exists between adjacent windings of the spirally wound wire rod in a state in which no external force is applied. However, it is also possible that the coil 4 can be constructed to have a form different than that shown so that the adjacent windings of the spirally wound wire rod are disposed close to one another (in contact with one another) without a gap when no external force is applied.

The coil 4 is preferably made of a metal material. In the present embodiment, examples of the metal material of the coil 4 include stainless steel, superelastic alloys, cobalt based alloys, noble metals such as gold, platinum and tungsten or alloys containing such noble metals. Particularly where the coil 4 is made of a non-radiolucent material such as a noble metal, the guide wire 1 possesses a radiopaque property and so it is possible to insert the guide wire 1 into a living organism while the position of the distal portion of the guide wire 1 is confirmed under radioscopy, which is preferable. Also, the distal side portion and the proximal side portion of the coil 4 may be made of different materials. For example, the distal side portion and the proximal side portion of the coil 4 may be formed separately such that the distal side portion is formed from a coil of a non-radiolucent material while the proximal side portion is formed from a coil of a material (stainless steel or the like) which is comparatively radiolucent. Although the overall length of the coil 4 is not limited to any particular length, it preferably is approximately 5 to 500 mm.

In this embodiment, the proximal portion and the distal portion of the coil 4 are secured to the first wire 2 by fixation materials 11 and 12, respectively. Also, an intermediate portion of the coil 4 (i.e., a portion closer to the distal end than the proximal end) is secured to the first wire 2 by a fixation material 13. The fixation materials 11, 12, 13 are made of solder (wax) or adhesive. In the present embodiment, the securing method for the coil 4 is not limited to fixation with a fixation material, but may be accomplished by welding. Further, in order to prevent damage to the inner wall of a blood vessel, preferably the distal face of the fixation material 12 is somewhat rounded.

By virtue of the coil 4 described above, the first wire 2 is covered with the coil 4 and has a relatively small contact area. Therefore, the sliding resistance is reduced and the steerability of the guide wire 1 is further improved.

The coil 4 used in the illustrated embodiment of the guide wire is made of a wire rod having a circular cross-section. However, the coil 4 is not limited in this regard as it may alternatively be in the form of a wire rod possessing other cross-sectional shapes such as an elliptic cross-sectional shape, a quadrangular cross-sectional shape (particularly rectangular shape).

The guide wire 1 as described above is configured such that the intermediate member 14 is disposed between the first wire 2 and the second wire 3, with the intermediate member 14, the first wire 2 and the second wire 3 welded to each other to connect the first wire 2 and the second wire 3 to each other. Consequently, the connecting portion between the first wire 2 and the second wire 3 is provided with high coupling strength (bonding strength), and so the guide wire 1 is able to reliably transmit torsional torque or pushing force from the second wire 3 to the first wire 2.

At the connecting portion, the intermediate member 14 interposed between the first wire 2 and the second wire 3 joins the first wire 2 and the second wire 3 together with the bonding strength at the atom (atomic) level based on formation of a solid solution or compound by welding or diffusion of the atoms. Consequently, the first wire 2 and the second wire 3 are connected to each other firmly.

Conventional guide wires are known in which a first wire and a second wire are soldered to each other. However, since the solder used has a low mechanical characteristic, when the guide wire is curved, there is the possibility that the soldered portion may be broken or bent.

In contrast, in the guide wire here, the first wire 2 and the second wire 3 are welded to each other by way of the intermediate member 14 which is used to connect the first wire 2 and the second wire 3. The intermediate member 14 employed here contains at least one metal component from among Pd, Pt, Rh, Ir and Ta.

An intermediate member 14 as just described is, by itself, superior in mechanical characteristic such as flexural strength. Thus, the guide wire 1 in which the intermediate member 14 is used to connect the first wire 2 and the second wire 3 to each other exhibits sufficient durability during curving operations or maneuvers.

The metal component contained in the intermediate member 14 as described above cooperates with many other metal components to produce a solid solution or compound. In particular, the metal component is superior in terms of its compatibility with many other metal components. Therefore, while production of fragile intermetallic compound is suppressed, the intermediate member 14 and the first wire 2 and the second wire 3 can be welded firmly based on the coupling that occurs at the atomic level without depending upon the component materials of the first wire 2 and the second wire 3. As a result, the first wire 2 and the second wire 3 can be connected to each other rather firmly.

The connection end face 21 of the first wire 2 and the connection end face 31 of the second wire 3 are individually connected in an abutting relationship to the intermediate member 14. Compared to, for example, an alternative configuration in which the first wire and the second wire are connected to each other through a sleeve which continuously covers the outer periphery of the proximal portion of the first wire and the outer periphery of the distal portion of the second wire, variations in the outer diameter at the connecting portions can be minimized. Consequently, the sliding performance of the outer peripheral surface of the guide wire 1 can be increased. Further, if the outer diameter of the guide wire 1 is fixed or constant, improvement in the steerability of the guide wire 1 can be anticipated in that the guide wire 1 can be curved smoothly.

It is to be noted that the metal components Pd, Pt, Rh, Ir and Ta exhibit particularly noticeable compatibility with Fe, Ni and Ti. Accordingly, where the first wire 2 and the second wire 3 individually contain at least one of Fe, Ni and Ti, the first wire 2 and the second wire 3 can be welded more firmly to the intermediate member 14.

In such an intermediate member 14 as described above, the total content of at least one metal component from among Pd, Pt, Rh, Ir and Ta is suitably set in accordance with the composition of the other metal components contained in the intermediate member 14.

In particular, in the intermediate member 14, the total content of at least one metal component from among Pd, Pt, Rh, Ir and Ta preferably is approximately 0.1 to 99 atom %, and more preferably is approximately 3 to 90 atom %. In this way, even if the intermediate member 14 is a wire having a bonding face of a relatively small area, it is possible to firmly connect the first wire 2 and the second wire 3 to each other. In addition, the mechanical characteristics of the intermediate member 14 are sufficiently high. Accordingly, the guide wire 1 provided with such an intermediate member 14 as just described exhibits sufficient durability during a curving operation (manipulation during use through complicatedly curved vessels) and has a relatively high degree of reliability.

Preferably the intermediate member 14 further contains a material which functions to lower the melting point of the intermediate member 14. With an intermediate member 14 containing such a material which lowers the melting point of the intermediate member 14, welding can be carried out at a lower temperature. Consequently, welding can be carried out safely and at a relatively low cost.

Further, if the melting point of the intermediate member 14 is lowered, then welding can be carried out while the thermal load applied to the first wire 2 or the second wire 3 is reduced or suppressed. Therefore, it is possible to reduce the possibility of deteriorating the first wire 2 and/or the second wire 3 by heat, and/or increase the selection of materials for the first wire 2 and/or the second wire 3.

Materials which can be used to lower the melting point of the intermediate member 14 as just described can include any material which has the capability of functioning to lower the melting point. However, it is particularly preferable to use at least one of Mg, Au, Ag, Cu, Ca and Li. These metals are well suited to lowering the melting point of the intermediate member 14 without adversely affecting other advantageous characteristics of the intermediate member 14 as described above.

In situations where the first wire and the second wire forming a guide wire individually contain at least one of Ti and Cr, conventionally there has been a problem in that it is particularly difficult to solder or weld the first wire and the second wire.

Ti and Cr react with oxygen in the atmospheric air to produce oxides such as $TiO_2$ and $Cr_2O_3$, and form a film which is chemically very stable. Therefore, a problem as described above is caused by the fact that the first wire and the second wire which contain at least one of Ti and Cr have an oxide film on the surface thereof which is exposed to the atmospheric air. In other words, the problem described above is caused by the fact that wetting of the solder or diffusion of atoms upon welding is obstructed by the oxide film.

Where this problem is taken into consideration, the intermediate member 14 preferably contains a metal having an ionization tendency higher than that of Ti and Cr. This reference to a metal having an ionization tendency higher than that of TI and Cr refers to a metal having a higher ionization tendency than Ti and Cr and capable of being ionized more readily than Ti and Cr.

At the bonding interfaces between the intermediate member 14 containing a metal as just described and the first and second wires 2, 3, the metal having a base ionization tendency acts upon the oxide film and can take oxygen electrons from oxides such as $TiO_2$ or $Cr_2O_3$ to reduce the oxides. Consequently, the oxide film is removed (reformed) to allow the intermediate member 14 and the base materials of the first wire 2 and the second wire 3 to react directly with each other. As a result, since the intermediate member 14 and the first wire 2 and second wire 3 can be welded more firmly, it is possible to obtain a guide wire 1 of relatively high reliability in which the first wire 2 and the second wire 3 each having an oxide film on the surface thereof are connected to each other rather firmly.

Examples of metals having a higher ionization tendency than Ti and Cr for use in making the intermediate member 14 include Li, Cs, Rb, K, Ba, Sr, Ca, Na, La, Mg. These materials can be used individually in the intermediate member 14, or two or more ones of them can be used in combination. However, Mg is particularly preferable. Mg is comparatively less expensive and can be obtained relatively easily. Further, Mg has an advantage also in that, when it reacts with another metal, it is less likely to produce a hard and friable ion bonded substance. Therefore, the first wire 2 and the second wire 3 can be connected further firmly, and the formed intermediate member 14 is comparatively superior in toughness. From the materials mentioned above, Mg is considered suitable as a component of the intermediate member 14.

It is noted that Mg also has an ability (functionality) of lowering the melting point of the intermediate member 14 as described above. Accordingly, if the intermediate member 14 contains Mg, the intermediate member 14 and the first and second wires 2, 3 can be individually welded rather firmly to each other. In addition, the welding can be carried out relatively safely and at a relatively low cost.

Further, the intermediate member 14 is preferably made of a eutectic type alloy having a eutectic point composition. Since the melting point of the intermediate member 14 made of a eutectic type alloy becomes considerably lower if the composition is selected in the proximity of the eutectic point, the intermediate member 14 and the first wire 2 and the second wire 3 can be individually welded rather safely and at a relatively low cost as described hereinabove.

From such points of view as described above, the intermediate member 14 made of a eutectic type alloy has a composition in the proximity of the eutectic point.

More particularly, the eutectic point composition, for example, of a Pd—Mg alloy is a composition of 7.8 atom % Pd-92.2 atom % Mg.

Taking this into consideration, the content of Mg in the intermediate member 14 made of a Pd—Mg alloy preferably is approximately 87 to 97 atom % and more preferably is approximately 89 to 95 atom %. If the content of Mg in the intermediate member 14 is set within the range given above, the removing action of an oxide film by Mg can be exhibited sufficiently, and the intermediate member 14 and the first wire 2 and the second wire 3 can be individually welded to each other firmly. In addition, since the melting point of the intermediate member 14 becomes particularly low, there is an advantage also in that the intermediate member 14 and the first wire 2 and second wire 3 can be welded particularly safely and at a rather low cost. Further, the guide wire 1 which includes such an intermediate member 14 as described above is superior in mechanical characteristic and is high in reliability.

As a further example, the eutectic point composition of an Ir—Mg alloy is a composition of 3.2 atom % Ir-96.8 atom % Mg.

Taking this into consideration, the content of Mg in the intermediate member 14 made of an Ir—Mg alloy preferably is approximately 93 to 99.9 atom %, and more preferably is approximately 95 to 97 atom %. With the intermediate member 14 satisfying the condition just described, similar action and effects to those in the case of a Pd—Mg alloy described hereinabove can be obtained.

Although the melting point of such an intermediate member 14 as described above is not restricted to a particular temperature, it is preferably approximately 500 to 1,350° C. If the melting point of the intermediate member 14 is within the range given above, when the intermediate member 14 and the first wire 2 and second wire 3 are individually welded, the influence (degeneration, deterioration or fusion) of heat of welding on the first wire 2 and the second wire 3 can be moderated. Consequently, the guide wire 1 obtained has relatively high reliability.

Further, in the present embodiment, the connection end face 21 of the first wire 2 to the intermediate member 14, and the connection end face 31 of the second wire 3 to the intermediate member 14, individually exhibit planes perpendicular to the axial direction (longitudinal direction) of both wires. Consequently, the work associated with forming the connection end faces 21, 31 is rather easy, and the effects described above can be achieved without complicating the fabrication process of the guide wire 1.

Though the connection end faces 21, 31 are illustrated as preferably being in planes perpendicular to the axis of the wires, it is to be noted that the connection end faces 21, 31 may otherwise be inclined with respect to a plane perpendicular to the axial direction (longitudinal direction) of the two wires, or may be formed as concave faces or convex faces. Since this increases the area of the faces (connection end faces) which contribute to welding, the first wire 2 and the second wire 3 can be welded more firmly.

The method of welding the first wire 2 and second wire 3 and the intermediate member 14 individually is not particularly limited. For example, laser welding using a laser, butt resistance welding such as upset welding, arc welding using arc discharge, gas welding using a torch which radiates gas flame, electron beam welding using an electron beam can be used.

Referring to FIG. 3, set forth below is a description of steps (1) to (4) which can be employed for welding the first wire 2, the second wire 3 and the intermediate member 14. In this example, the first wire 2, the second wire 3 and the intermediate member 14 are laser welded.

As illustrated in FIG. 3, at step (1), the first wire 2 and the second wire 3 are fixed in position, in a spaced apart relationship to one another in which the first and second wires are spaced apart a predetermined distance, by suitable fixtures.

At step (2), the intermediate member 14 is positioned between the first wire 2 and the second wire 3 and is then held in position by the first and second wires. Consequently, the connection end face (proximal most end) 21 of the first wire 2 contacts the distal most end of the intermediate member 14, and the connection end face (distal most end) 31 of the second wire 3 contacts the proximal most end of the intermediate member 14.

At step (3), the contact interface (connection end face 21) between the first wire 2 and the intermediate member 14 and the contact interface (connection end face 31) between the second wire 3 and the intermediate member 14 are individually irradiated in predetermined conditions by a laser beam. Consequently, the intermediate member 14 and the first wire 2, and the intermediate member 14 and the second wire 3 are individually welded firmly based on chemical bonding. Consequently, connection portions 140 are formed.

Further, as occasion demands, a radially outwardly projected projecting portion on the outer peripheral surface of the connection portions 140 which may result following the welding process, is preferably removed. The outer periphery of the connection portions 140 are thus substantially smoothed. The removing method for removing the projecting portion or smoothing the outer surface of the connection portions 140 can involve, for example, mechanical working such as grinding or polishing, and chemical processing such as etching.

At step (4), a portion of the first wire 2 on the distal side with respect to the connection portions 140 is ground, polished or otherwise processed to form the outer diameter gradually decreasing portion 15 whose outer diameter gradually decreases in a direction toward the distal.

The first wire 2 and the second wire 3 are thus connected to each other in the manner described above.

It is to be noted that the first wire 2 and the intermediate member 14 may be bonded or connected to one another by welding, while the second wire 3 and the intermediate member 14 are bonded or connected by a method other than welding, for example by soldering.

Alternatively, the second wire 3 and the intermediate member 14 may be connected or bonded by welding, while the first wire 2 and the intermediate member 14 are bonded or connected by a method other than welding, for example by soldering.

A coating layer 5 covers a portion of, or the entirety of, the outer peripheral surface of the wire body 5. The coating layer 5 can be selected and provided for purposes of achieving certain desirable results. For example, the coating layer can be selected to improve the steerability of the guide wire 1 by reducing the friction (sliding resistance) of the guide wire 1, thus improving the sliding performance of the guide wire 1.

To achieve such a result, the coating layer 5 is preferably made of a material which can reduce the friction. In this way, the frictional resistance (sliding resistance) with the inner wall of a catheter used together with the guide wire 1 is reduced to improve the sliding performance, and the steerability of the guide wire 1 in the catheter becomes better. Further, since the sliding resistance of the guide wire 1 is decreased, when the guide wire 1 is moved and/or rotated in the catheter, kinking (bending) or twisting of the guide wire 1, particularly kinking or twisting in the proximity of the connection portions 140, can be prevented with relative reliability.

Examples of material which can reduce friction as described above include and which can be used as the coating layer 5 include polyolefin such as polyethylene or polypropylene, polyvinyl chloride, polyester (PET, PBT or the like), polyamide, polyimide, polyurethane, polystyrene, polycarbonate, silicone resins, fluorocarbon resins (PTFE, ETFE or the like) and composites or combinations of such materials.

Particularly where a fluorocarbon resin (or a composite material which contains a fluorocarbon resin) is used, the frictional resistance (sliding resistance) between the guide wire 1 and the inner wall of the catheter can be reduced more effectively to improve the sliding performance. Consequently, the steerability of the guide wire 1 in the catheter becomes better. Further, when the guide wire 1 is moved and/or rotated in the catheter, kinking (bending) or twisting of the guide wire 1, particularly kinking or twisting in the proximity of the connection portions 140, can be relatively reliably prevented.

Further, where a fluorocarbon resin (or a composite material which contains a fluorocarbon resin) is used, in a state wherein the resin material is heated, coating of the resin material on the wire body 10 can be performed by such a method as baking or spraying. In this way, the adhesion of the wire body 10 to the coating layer 5 becomes particularly excellent.

Alternatively, where the coating layer 5 is made of a silicone resin (or a composite material which contains a silicone resin), when the coating layer 5 is formed (coated on the wire body 10), even if it is not heated, it is possible to achieve a coating layer 5 which contacts closely with the wire body 10 with relative certainty. In particular, where the coating layer 5 is formed from a silicone resin (or a composite material which contains a silicone resin), since a material of the reaction curing type or a like material can be used, formation of the coating layer 5 can be performed at room temperature. By forming the coating layer 5 at room temperature in this manner, the coating can be performed simply and conveniently, and the guide wire 1 can be steered in a state wherein the bonding strength at the connection portions 140 between the first wire 2 and the second wire 3 is sufficiently maintained.

Another preferable example of a material which can reduce friction and which can be used for the coating layer includes a hydrophilic material or a hydrophobic material. Among them, particularly a hydrophilic material is preferable.

Examples of hydrophilic materials which can be used as the coating layer 5 include cellulose based high molecular substances, polyethylene oxide based high molecular substances, maleic anhydride based high molecular substances (for example, maleic anhydride copolymer such as methyl vinyl ether-maleic anhydride copolymer), acrylamide based high molecular substances (for example, polyacrylamide, block copolymer of polyglycidyl methacrylate-dimethylacrylamide (PGMA-DMAA)), water-soluble nylon, polyvinyl alcohol, and polyvinyl pyrrolidone.

Such hydrophilic materials as listed above in most cases exhibit lubricity when they are wetted (absorb water), and reduce the frictional resistance (sliding resistance) with a catheter used together with the guide wire 1. Consequently, the sliding performance of the guide wire 1 is improved, and the steerability of the guide wire 1 in the catheter becomes better.

The site of formation of the coating layer 5 as described above may be the entire length or longitudinal extent of the wire body 10, or may be a part of the length or longitudinal extent of the wire body 10. However, the coating layer 5 is preferably formed to cover at least the connection portions 140, that is, a portion of the wire body 10 that includes at least the connection portions 140. In this way, even if a shoulder, burr or the like should appear at the outer peripheral portion of the connection portions 140, since this is covered with the coating layer 5, the sliding performance is not significantly adversely affected. Further, since the coating layer 5 possesses or provides a uniform or constant outer diameter (inclusive of substantially uniform or constant), the sliding performance is further improved.

The thickness of the coating layer 5 is not particularly limited. However, the thickness (average) is preferably approximately 1 to 20 µm, and more preferably approximately 2 to 10 µm. If the thickness of the coating layer 5 is excessively small, the intended purpose severed by the coating layer 5 may not be exhibited or realized sufficiently, and it is possible that exfoliation of the coating layer 5 may occur. On the other hand, if the thickness of the coating layer 5 is excessively large, the physical properties of the wire may be disturbed or undesirably affected, and exfoliation of the coating layer 5 may occur.

It is possible to apply a process (chemical processing, heat processing or the like) for improving the adhesion of the coating layer 5 to the outer circumferential surface of the wire body 10, or to provide an intermediate layer suitable for improving the adhesion of the coating layer 5.

A second embodiment of the guide wire disclosed here is illustrated in FIG. 4. The description of this second embodiment will primarily focus on features of the second embodiment that differ relative to the first embodiment described above. Features in this second embodiment that are the same as those described above are designated by the same reference numeral, and a detailed description of such features is not repeated.

In this second embodiment, the first wire and the second wire connected by the intermediate member such as described above are constituted by the first wire 2 and the coil 4. In particular, in the guide wire 1 according to this embodiment, the first wire 2 and the coil 4 are individually welded to an intermediate member in a manner similar to that described above, wherein the intermediate member is similar in composition to the intermediate member described above which connects the first and second wires (i.e., the first wire 1 and the second wire 2 forming the wire body 10).

Here, in the guide wire 1 according to this second embodiment, the first wire 2 is made principally of a first metal material that is the same as in the first embodiment described above. The coil 4 is made principally of the above-described second metal material that is different in composition from the first metal material. In other words, the coil 4 in this embodiment is made of the same metal material as the second metal material used to fabricate the second wire 2 in the first embodiment described above.

This coil 4 is secured to the first wire 2 through intermediate members 16, 17, 18. In particular, the intermediate members 16, 17, 18 and the coil 4 and the first wire 2 are welded to each other. Each of the intermediate members 16, 17, 18 is formed from material that is the same as the material(s) forming the intermediate member 14 as described above. By using such intermediate members 16, 17, 18 formed of the intermediate member material(s) described above, the first wire 2 and the coil 4 can be connected to each other rather firmly using the laser welding method described above. As a result, the guide wire 1 having a high degree of reliability is obtained.

In this illustrated embodiment, the first wire 2 and the coil 4 are secured to each other through three intermediate members 16, 17, 18 (intermediate members as disclosed herein), wherein the intermediate members are fabricated in accordance with the disclosure contained herein and are connected to the first and second wires 2, 4 in the manner described above. However, the guide wire here is not necessarily limited in that regard. For example, one or two of the three intermediate members 16, 17, 18 may be secured by any method, for example may be secured by a bonding agent or by a method such as soldering.

Further, in the guide wire 1 according to this embodiment, the first wire 2 is connected to the second wire 3 to form the wire body. The first and second wires 2, 3 may be connected (secured) to each other in the manner described above in the first embodiment (i.e., through the intermediate member 14) or may be secured together by other methods, for example may be connected by a method such as soldering or welding.

Further, in this present embodiment, the first wire 2 and the second wire 3 are connected to each other to form the wire body 10. However, it is also possible that the wire body 10 may be entirely formed from a single continuous material or may be formed by connecting three or more wire rods to each other. Where the wire body 10 is made of a single material, a preferable material is a Ni—Ti based alloy.

A third embodiment of the guide wire disclosed here is illustrated in FIG. 5. The description of this third embodiment will primarily focus on features of the third embodiment that differ relative to the first embodiment described above. Features in this third embodiment that are the same as those described above are designated by the same reference numeral, and a detailed description of such features is not repeated.

In the present embodiment, an intermediate member 14' has a shape of a pipe or a cylindrical member. The pipe-shaped intermediate member 14' covers, in a state wherein the proximal end face of the first wire 2 is disposed adjacent the distal end face of the second wire 3, the outer peripheral surface of the boundary portions of the first and second wires 2, 3. In other words, the intermediate member 14' extends from the proximal end of the first wire 2 to the distal end of the second wire 3. In the illustrated embodiment, the cylindrically-shaped intermediate member 14' extends distally beyond the proximal end face of the first wire 2 and proximally beyond the distal end face of the second wire 3.

In this state, the first wire 2 and the intermediate member 14' are joined together by welding, and the second wire 3 and the intermediate member 14' are joined together by welding. As shown in FIG. 5, melted portions 19 are formed such that they extend through the intermediate member 14' such that part of the first wire 2 and part of the second wire 3 are melted in a radial direction. Consequently, the first wire 2 and the second wire 3 are connected to each other through the intermediate member 14'.

The composition of the material for the intermediate member 14' is similar to that of the intermediate member 14 in the first embodiment described above.

Further, a portion of the first wire 2 which is covered by the intermediate member 14' preferably has an outer diameter smaller than that of an adjoining portion of the first wire. In particular, the proximal end portion of the first wire 2 possesses an outer diameter smaller than the outer diameter of the portion of the first wire 2 adjoining the proximal end portion of the first wire 2. Similarly, a portion of the second wire 3 which is covered by the intermediate member 14' preferably has an outer diameter smaller than that of the adjoining portion of the second wire 3. In particular, the distal end portion of the second wire 3 possesses an outer diameter smaller than the outer diameter of the portion of the second wire 3 adjoining the distal end portion of the second wire 3. This construction makes it less likely that a shoulder exists between the outer circumferential surface of the intermediate member 14' and the outer circumferential surfaces of the first wire 2 and the second wire 3. In other words, since a shoulder is less likely to exist on the outer circumference of the guide wire 1, deterioration of the sliding performance of the guide wire 1 is inhibited or prevented.

In the illustrated embodiment, the decreased (smaller) outer diameter of the proximal end portion of the first wire 2 and the decreased (smaller) outer diameter of the distal end portion of the second wire 3 is preferably equal (inclusive of substantially equal) to the thickness of the intermediate member 14'. In other words, the outer diameter of the cylindrically-shaped intermediate member 14' is equal (inclusive of substantially equal) to both the outer diameter of the portion of the first wire 2 adjoining the reduced outer diameter proximal end portion of the first wire and the outer diameter of the portion of the second wire 3 adjoining the reduced outer diameter distal end portion of the second wire 2. By virtue of this construction, the effects described above are exhibited more notably.

The intermediate member 14' can be connected to the first wire 2 and the second wire 3 using the various welding methods described above in connection with the first embodiment. However, it is preferable to use laser welding. Through use of laser welding, welding in a relatively small area (spot welding) can be performed. Further, with laser welding, it is relatively easy to adjust the melting depth upon welding. It is thus possible to avoid a situation in which a melted portion 19 extends through the first wire 2 or the second wire 3.

The guide wire 1 according to the third embodiment as described above can achieve results and effects similar to those of the first embodiment described above.

While the guide wire and intermediate member disclosed here have been described based on the embodiments shown in the drawings, the present invention is not limited to the particular constructions as illustrated and described. Components of the guide wire can be replaced by other components which exhibit similar characteristics and/or functions. Further, additional features can be incorporated into the guide wire.

Further, the guide wire can be configured to include a combination of the configurations described in connection with the various embodiments. For example, the guide wire can be constructed so that the first wire 2 and the second wire 3 are connected or secured to each other using the intermediate member disclosed herein, and so that the first wire 2 and the coil 4 are secured or connected to each other using the intermediate member disclosed herein.

Also, a configuration involving a combination of the first embodiment and the third embodiment may be used.

Further, in the embodiments described above, the first wire and the second wire which are connected using the intermediate member disclosed here are described by way of example in the context of a first wire and a second wire forming the wire body, as well as a first wire and a coil. Other examples of the first wire and the second wire include a part of eyeglasses, and a straightening part for dental use. Also where such parts are connected using the intermediate member disclosed herein, advantages and effects similar to those described above are achieved.

EXAMPLES

Specific examples of the guide wire utilizing the intermediate member disclosed herein are described below.

1. Fabrication of the Guide Wire

Example 1

A first wire and a second wire shown in FIG. 1 were prepared. The first wire is made of an alloy of 50 atom % Ni-50 atom % Ti, and the second wire is made of a stainless steel, specifically type 304 stainless steel.

The first and second wires were disposed using fixtures such that the connection end face of the first wire and the connection end face of the second wire were opposed to each other, and an intermediate member was inserted between the connection end faces of the first and second wires. The composition of the intermediate member used is specified in Table 1 below.

Then, a laser welding machine was used to irradiate or direct a laser beam upon the contact interface between the first wire and the intermediate member, and upon the contact interface between the second wire and the intermediate member to perform welding. Consequently, the first wire and the second wire were connected to each other. Following the welding, the outer periphery of the connection portion was smoothed by machining.

Thereafter, to complete the fabrication of the guide wire, the distal side of the first wire was ground to form an outer diameter gradually decreasing portion whose outer diameter gradually decreases in a direction toward the distal end.

Examples 2 to 11

Guide wires were fabricated similar to that of Example 1 described above, except that the composition of the intermediate member used was changed in the manner shown in Table 1.

Comparative Example 1

A guide wire was fabricated similar to that of Example 1, except that a solder material made of an alloy of 72 atom % Ag-28 atom % Cu was used to solder the first wire and the second wire to each other.

Comparative Example 2

A guide wire was fabricated similar to that of Example 1, except that the first wire and the second wire were welded directly to each other.

TABLE 1

| | Composition of intermediate member [atom %] | | | | | |
|---|---|---|---|---|---|---|
| | Pd | Pt | Rh | Ir | Ta | Mg |
| Example 1 | 13 | — | — | — | — | 87 |
| Example 2 | 7.8 | — | — | — | — | 92.2 |
| Example 3 | 3 | — | — | — | — | 97 |
| Example 4 | 50 | — | — | — | — | 50 |
| Example 5 | — | 50 | — | — | — | 50 |
| Example 6 | — | — | 50 | — | — | 50 |
| Example 7 | — | — | — | 7 | — | 93 |
| Example 8 | — | — | — | 3.2 | — | 96.8 |
| Example 9 | — | — | — | 1 | — | 99 |
| Example 10 | — | — | — | 50 | — | 50 |
| Example 11 | — | — | — | — | 50 | 50 |
| Comparative Example 1 | First wire and second wire are soldered by Ag—Cu solder | | | | | |
| Comparative Example 2 | First wire and second wire are welded directly | | | | | |

2. Evaluation 2.1 Evaluation of Curvability

The guide wires in Examples 1-11 and in Comparative Examples 1 and 2 were operated so as to be curved, and the appearance of the guide wires then was evaluated through visual observation.

The evaluation results for Examples 1-11 of the guide wire show that even if the guide wires were curved, they were able to be operated so as to be curved into a smooth shape while maintaining a fixed curvature without suffering from buckling.

On the other hand, with the guide wire obtained in Comparative Example 1, the guide wire was bent at the connection portion between the first wire and the second wire, resulting in failure to perform a desired curving operation.

Further, with the guide wire obtained in Comparative Example 2, when it was curved, the first wire and the second wire were separated from each other.

2.2 Evaluation of Flexural Strength

Using the three point bending test, the flexural strength was measured with regard to the connection portion of the guide wires obtained in Examples 1-11 and in Comparative Examples 1 and 2.

The results show that the connection portions of the guide wires in Examples 1-11 were all superior in flexural strength compared to the connection portions of the guide wires in Comparative Examples 1 and 2.

The principles, embodiments and operational aspects of the guide wire and intermediate member disclosed here have been described in the foregoing specification, but the invention which is intended to be protected is not to be construed as limited to the particular embodiments disclosed. The embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A guide wire comprising;
an elongated wire body and a coil covering at least a distal portion of the elongated wire body;
the elongated wire body comprising a first wire member and a second wire member that are coaxially positioned relative to one another;
the first wire member being made of a metal material;
the second wire member being made of a metal material having a composition different from the composition of the metal material forming the first wire member;
the coil being made of a metal material having a composition different from the composition of the metal material forming the first wire member;
an intermediate member disposed either between the first wire member and the second wire member and connecting the first and second wire members to each other, or between the first wire member and the coil and connecting the coil to the first wire member;
the intermediate member comprising at least one of Pd, Pt, Rb, Ir and Ta;
the metal material forming the first wire member containing at least one of Ti and Cr as a principal component;
the metal material forming the second wire member containing at least one of Ti an Cr as a principal component;
the intermediate member containing a metal having an ionization tendency higher than that of Ti and Cr;
the metal having the ionization tendency higher than that of Ti and Cr is Mg; and
wherein a content of magnesium in the intermediate member is approximately 87 atom % to 99.9 atom %.

2. The guide wire according to claim 1, wherein:
the second wire member is proximally positioned relative to the first wire member; and
the intermediate member is positioned between a proximal end face of the first wire member and a distal end face of the second wire member so that the first wire member and the second wire member are connected to each other by the intermediate member.

3. The guide wire according to claim 1, wherein:
the second wire member is proximally positioned relative to the first wire member;
the intermediate member is positioned between the first wire member and the coil so that the coil is connected to the first wire member by the intermediate member.

4. The medical device according to claim 1, wherein the first wire member possesses a proximal end face and the second wire member possessing a distal end face, the proximal end face of the first wire member and the distal end face of the second wire member facing one another, and the intermediate member being disposed between the first wire member and the second wire member and connecting the first and second wire members to each other so that a longitudinal axis of the elongated wire body intersects the first wire member, the second wire member and the intermediate member.

5. The medical device according to claim 1, wherein the intermediate member is a first intermediate member disposed between the first wire member and the coil and connecting the coil to the first wire member, and further comprising at least one additional intermediate member disposed between the first wire member and the coil and connecting the coil to the first wire member, the additional intermediate member being made of the same material as the first intermediate member, the additional intermediate member being spaced from the first intermediate member along a longitudinal extent of the elongate wire body so that the additional intermediate member is not in contact with the first intermediate member.

6. The guide wire according to claim 1, wherein the intermediate member is comprised of an eutectic type alloy having an eutectic point composition.

7. A guide wire comprising;
a first member made of a first metal material;
a second member made of a second metal material and having a composition different from the composition of the first metal material of the first member;
the first member being connected to the second member by way of an intermediate member;
the intermediate member containing at least one metal component;
the at least one metal component being Pd, Pt, Rb, Ir or Ta;
the metal material forming the first wire member containing at least one of Ti and Cr as a principal component;
the metal material forming the second wire member containing at least one of Ti and Cr as a principal component;
the intermediate member containing a metal having an ionization tendency higher than that of Ti and Cr;
the metal having the ionization tendency higher than that of Ti and Cr is Mg; and
wherein the intermediate member is made of a Pd—Mg alloy, and a content of Mg in the Pd—Mg alloy is 87 to 97 atom %.

8. A medical device comprising:
a first member made of a first metal material having a composition;
a second member made of a second metal material having a composition different from the composition of the first metal material;
an intermediate member positioned between the first member and the second member;
the intermediate member being welded to the first member and the second member to connect the first member and the second member to each other;
the intermediate member containing at least one metal component, and wherein the one metal component is Pd, Pt, Rb, Ir or Ta;
the intermediate member further containing a melting point lowering material which lowers a melting point of the intermediate member;
the melting point lowering material being at least one of Mg, Au, Ag, Cu, Ca and Li;
the intermediate member further containing a metal having an ionization tendency higher than that of Ti and Cr;
the metal having the ionization tendency higher than that of Ti and Cr is Mg; and
wherein the intermediate member is made of a Pd—Mg alloy, and a content of Mq in the Pd—Mg alloy is 87 to 97 atom %.

9. The medical device according to claim 8, wherein the metal component in the intermediate member has a total content of 0.1 to 99 atom %.

10. The medical device according to claim 8, wherein the first metal material and the second metal material individually contain at least one of Fe, Ni and Ti.

11. The medical device according to claim 10, wherein the first metal material is made of a Ni—Ti based alloy.

12. The medical device according to claim 10, wherein the second metal material is made of stainless steel.

13. The medical device according to claim 8, wherein:
the first metal material and the second metal material individually contain at least one of Ti and Cr as a principal component; and
the intermediate member further contains a metal having an ionization tendency higher than that of Ti and Cr.

14. The medical device according to claim 8, wherein the intermediate member possesses a melting point of 500 to 1,350° C.

15. The medical device according to claim 8, wherein one of the first member and the second member is a first wire disposed on the distal side, and the other is a second wire disposed on the proximal side of the first wire.

16. The medical device according to claim 8, wherein one of the first member and the second member is a wire body, and the other is a spiral coil which covers a distal portion of the wire body.

17. A medical device comprising:
a first member made of a first metal material having a composition;
a second member made of a second metal material having a composition different from the composition of the first metal material;
an intermediate member positioned between the first member and the second member;
the intermediate member being welded to the first member and the second member to connect the first member and the second member to each other;
the intermediate member containing at least one metal component;
the one metal component is Pd, Pt, Rb, Ir or Ta; and
wherein the intermediate member is made of one of a Pd—Mg alloy and an Ir—Mg alloy, and a content of Mg in the Pd—Mg alloy is 87 to 97 atom % or a content of Mg in the Ir—Mg alloy is 93 to 99.9 atom %.

18. A medical device comprising:
a first member made of a first metal material having a composition;
a second member made of a second metal material having a composition different from the composition of the first metal material;
an intermediate member positioned between the first member and the second member;
the intermediate member being welded to the first member and the second member to connect the first member and the second member to each other;
the intermediate member containing at least one metal component, and wherein the one metal component is Pd, Pt, Rb, Ir, or Ta;
the intermediate member further containing a melting point lowering material which lowers a melting point of the intermediate member;
the melting point lowering material being at least one of Mg, Au, Ag, Cu, Ca and Li;
the intermediate member further containing a metal having an ionization tendency higher than that of Ti and Cr;
the metal having the ionization tendency higher than that of Ti and Cr is Mg; and
wherein the intermediate member is made of a Ir—Mg alloy, and a content of Mg in the Ir—Mg alloy is 93 to 99.9 atom %.

* * * * *